US012780796B2

(12) United States Patent
Trippeer et al.

(10) Patent No.: US 12,780,796 B2
(45) Date of Patent: Nov. 3, 2026

(54) PROCESSES FOR THE PREPARATION OF CERTAIN MESOIONIC PESTICIDES

(71) Applicant: CORTEVA AGRISCIENCE LLC, Indianapolis, IN (US)

(72) Inventors: Michael L. Trippeer, Brownsburg, IN (US); Chunming Zhang, Zionsville, IN (US); Chengli Zu, Carmel, IN (US)

(73) Assignee: CORTEVA AGRISCIENCE LLC, Indianpolis, IN (US)

( * ) Notice: Subject to any disclaimer, the term of this patent is extended or adjusted under 35 U.S.C. 154(b) by 351 days.

(21) Appl. No.: 18/708,365

(22) PCT Filed: Nov. 9, 2022

(86) PCT No.: PCT/US2022/079518

§ 371 (c)(1),
(2) Date: May 8, 2024

(87) PCT Pub. No.: WO2023/086802

PCT Pub. Date: May 19, 2023

(65) Prior Publication Data

US 2025/0011301 A1 Jan. 9, 2025

Related U.S. Application Data

(60) Provisional application No. 63/277,675, filed on Nov. 10, 2021, provisional application No. 63/373,216, filed on Aug. 23, 2022.

(51) Int. Cl.
*C07D 401/12* (2006.01)

(52) U.S. Cl.
CPC .................................. *C07D 401/12* (2013.01)

(58) Field of Classification Search
CPC .................................................... C07D 401/12
See application file for complete search history.

(56) References Cited

U.S. PATENT DOCUMENTS

| | | | |
|---|---|---|---|
| 9,108,965 | B2 | 8/2015 | Zhang |
| 12,356,988 | B2 | 7/2025 | Dumas et al. |
| 2005/0113437 | A1 | 5/2005 | McHardy et al. |
| 2007/0048217 | A1 | 3/2007 | McBride et al. |
| 2021/0051958 | A1 | 2/2021 | Dumas et al. |

FOREIGN PATENT DOCUMENTS

| | | | | |
|---|---|---|---|---|
| CN | 108373468 | A | 8/2018 | |
| CN | 111454247 | A | 7/2020 | |
| WO | 2005037790 | A1 | 4/2005 | |
| WO | 2007027385 | A2 | 3/2007 | |
| WO | 2009099929 | A1 | 8/2009 | |
| WO | 2013090547 | A1 | 6/2013 | |
| WO | WO-2023086802 | A1 * | 5/2023 | ........... C07D 401/12 |

OTHER PUBLICATIONS

Holyoke C. W., et al., "Mesoionic insecticides: A Novel Class of Insecticides That Modulate Nicotinic Acetylcholine Receptor," Pest Management Science, 2017, vol. 73, No. 4, pp. 796-806, DOI:10.1002/ps.4496, XP002775069.
International Search Report and Written Opinion for International Application No. PCT/US2022/079518, mailed Jan. 24, 2023, 8 Pages.
Berge S.M., et al., "Pharmaceutical Salts," Journal of Pharmaceutical Sciences, Jan. 1977, vol. 66, No. 1, pp. 1-19.
Butula, et al., "Aminoalkane Sulfonic Acids. V. The Synthesis of Some Antimitotic N-Nitroso-?-Amino-2-Pyridyl- and -2-Pyrimidinylalkanesulfonic Acids," Acta Pharmaceutica Jugoslavica, Apr. 1, 1984, vol. 34, No. 4, pp. 233-240, ISSN 0001-6667, XP009527503.
Butula L., "Aminoalkane Sulfonic Acids. Synthesis of Some Mitodepressive Heterocyclic Aminoalkane Sulfonic Acids," Die Pharmazie, Jul. 1, 1978, vol. 33, No. 7, pp. 428-430, ISSN 0031-7144, XP009527505.
Chemical Abstracts STN Registry Database, record for RN 1854713-07-7, a-hydroxy-5-pyrimidinemethanesulfonic acid, sodium salt, Entered STN Jan. 28, 2016.
Extended European Search Report for European Application No. 19763209.4, mailed May 31, 2021, 06 Pages.
Grygorenko O.O., et al., "Amino Sulfonic Acids, Peptidosulfonamides and Other Related Compounds", Tetrahedron, Feb. 20, 2018, vol. 74, pp. 1355-1421, XP085356227.
International Preliminary Report on Patentability for International Application No. PCT/US2019/020478, mailed Sep. 17, 2020, 10 Pages.
International Preliminary Report on Patentability for International Application No. PCT/US2023/072301, mailed Feb. 27, 2025, 6 Pages.
International Search Report and Written Opinion for International Application No. PCT/US2019/020478, mailed May 17, 2019, 12 Pages.
"Sodium;hydroxy(pyrimidin-5-yl)methanesulfonate | C5H5N2NaO4S," Database Accession No. 130923211, Pubchem Compound, Oct. 9, 2017, URL: NCBI, XP055637620.
Pandit C.R., et al., "Expedient Reductive Amination of Aldehyde Bisulfite Adducts," Synthesis, 2009, vol. 23, pp. 4032-4036, XP055637625.

* cited by examiner

*Primary Examiner* — Kevin E Weddington

(57) ABSTRACT

Processes to make intermediates to produce mesoionic pesticides are disclosed. Processes to produce N-(pyrimidin-5-ylmethyl)pyridin-2-amine, an important intermediate, are disclosed.

1 Claim, No Drawings

PROCESSES FOR THE PREPARATION OF CERTAIN MESOIONIC PESTICIDES

BACKGROUND FOR THIS DISCLOSURE

Mesoionic pesticides and methods for preparing them have been previously disclosed in, for example, WO 2009/099929 A1, WO 2011/017334 A1, WO 2011/017342 A1, WO 2011/017347 A1, WO 2011/017351 A1, WO 2012/092115 A1, WO 2013/090547 A1, WO 2017/189339 A1, and WO 2019/173173 A1. In addition, N-(pyrimidin-5-ylmethyl)pyridin-2-amine has been previously disclosed as an important intermediate for preparing certain mesoionic pesticides. However, certain synthesis steps disclosed previously may not be suitable for large-scale manufacture. Thus, there remains a need for alternative ways of preparing certain mesoionic pesticides.

DETAILED DESCRIPTION FOR THIS DISCLOSURE

The following are processes related to the formation of N-(pyrimidin-5-ylmethyl)pyridin-2-amine.

Scheme One is illustrated as follows

Scheme One

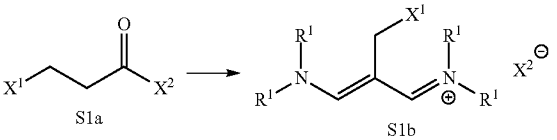

S1a S1b wherein $X^1$ is Cl, Br, or I;

$X^2$ is F, Cl, Br, I, or OH; and each $R^1$ is methyl, ethyl, or n-propyl.

In Scheme One, S1a, N,N-dialkyl formamide (hereafter "DAF") and oxalyl chloride ($(COCl)_2$), are mixed under conditions to produce S1b. In general, about 2 moles to about 20 moles of DAF per mole of S1a, preferably, about 3 moles to about 15 moles of DAF per mole of S1a, and more preferably, about 4 to about 10 moles of DAF per mole of S1a may be used. The N,N-dialkyl formamide may be N,N-dimethyl formamide, N,N-diethyl formamide, N,N-dipropyl formamide, and mixtures thereof. Also, about 0.5 moles to about 5 moles of oxalyl chloride per mole of S1a, preferably, about 0.8 moles to about 4 moles of oxalyl chloride per mole of S1a, and more preferably, about 1 to about 3 moles of oxalyl chloride per mole of S1a, may be used. In Scheme One, additional conditions comprise ambient temperatures and pressures. However, higher and lower temperatures and pressures may be used at different stages of the reaction. Currently, temperatures from about −10° C. to about 80° C. may be used; preferably temperatures from about −5° C. to about 60° C. may be used. Currently, pressures from about 10 kilopascals (kPa) to about 1000 kPa may be used; preferably pressures from about 50 kPa to about 150 kPa may be used.

In Scheme One, S1a may be 3-chloropropanoyl chloride, 3-chloropropanoyl bromide, 3-chloropropanoyl fluoride, 3-chloropropanoyl iodide, 3-bromopropanoyl chloride, 3-bromopropanoyl bromide, 3-bromopropanoyl fluoride, 3-bromopropanoyl iodide, 3-iodopropanoyl chloride, 3-iodopropanoyl iodide, 3-iodopropanoyl bromide, 3-chloropropanoic acid, 3-bromopropanoic acid, or 3-iodopropanoic acid. However, mixtures thereof may be used. More oxalyl chloride is used when the corresponding acid is used. Currently, 3-chloropropanoyl chloride is preferred. Other modifications to Scheme One may be used, such as, for example, using a substitute for oxalyl chloride. Such oxalyl chloride substitutes may be selected from phosphoryl chloride ($POCl_3$), thionyl chloride ($SOCl_2$), and phthaloyl chloride ($C_6H_4$-1,2-$(COCl)_2$). As another example, substitutes for N,N-dialkyl formamide may be used. Such N,N-dialkyl formamide substitutes may be piperidine-1-carbaldehyde, pyrrolidine-1-carbaldehyde, and morpholine-4-carbaldehyde.

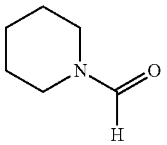

piperidine-1-carbaldehyde

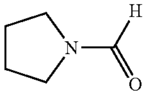

pyrrolidine-1-carbaldehyde

DAF substitutes

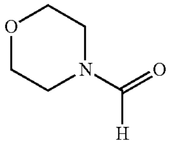

morpholine-4-carbaldehyde

However, when such DAF substitutes are used an S1b substitute is produced

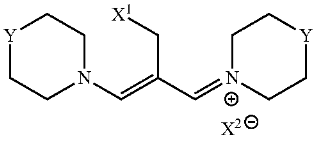

S1b-substitute wherein:

$X^1$ is Cl, Br, or I;

each Y is independently $(CH_2)_n$ or O; and n is 0 or 1.

Alternative Scheme One

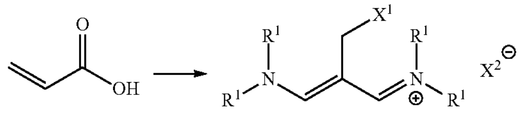

S1b

In Alternative Scheme One, acrylic acid, N,N-dialkyl formamide (hereafter "DAF") and oxalyl chloride ($(COCl)_2$), are mixed under conditions to produce S1b. In general, about 2 moles to about 20 moles of DAF per mole of acrylic acid, preferably, about 3 moles to about 15 moles of DAF per mole of acrylic acid, and more preferably, about 4 to about 10 moles of DAF per mole of acrylic acid may be used. The N,N-dialkyl formamide may be N,N-dimethyl formamide, N,N-diethyl formamide, N,N-dipropyl formamide, and mixtures thereof. However, it is preferred that about 1.5 moles to about 5 moles of oxalyl chloride per mole of acrylic acid, preferably, about 1.8 moles to about 4 moles of oxalyl chloride per mole of acrylic acid, and more preferably, about 2 to about 3 moles of oxalyl chloride per mole of acrylic acid, may be used. In Alternative Scheme One, additional conditions comprise ambient temperatures and pressures. However, higher and lower temperatures and pressures may be used at different stages of the reaction. Currently, temperatures from about −10° C. to about 80° C. may be used; preferably temperatures from about −5° C. to about 60° C. may be used. Currently, pressures from about 10 kilopascals (kPa) to about 1000 kPa may be used; preferably pressures from about 50 kPa to about 150 kPa may be used.

Other modifications to Alternative Scheme One may be used, such as, for example, using a substitute for oxalyl chloride. Such oxalyl chloride substitutes may be selected from phosphoryl chloride ($POCl_3$), thionyl chloride ($SOCl_2$), and phthaloyl chloride ($C_6H_4$-1,2-$(COCl)_2$).

Scheme Two is illustrated as follows

Scheme Two

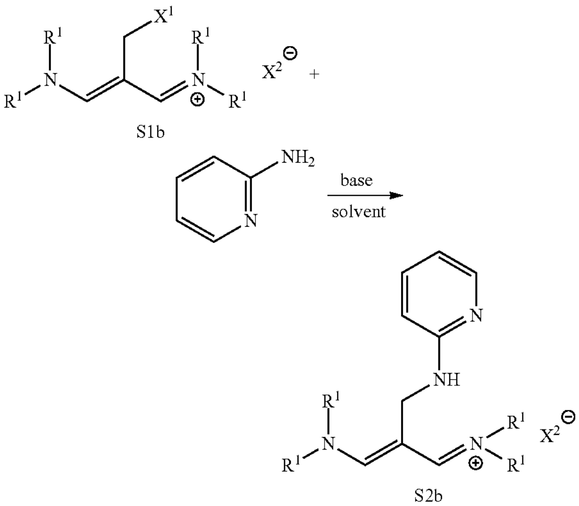

wherein $X^1$ is Cl, Br, or I; and each $R^1$ is methyl, ethyl, or n-propyl.

In Scheme Two, S1b, pyridine-2-amine (also known as 2-aminopyridine) and a base are mixed in the presence of a solvent under conditions to produce S2b. In general, about 0.8 moles to about 2 moles of pyridine-2-amine per mole of S1b, preferably, about 0.9 moles to about 1.8 moles of pyridine-2-amine per mole of S1b, and more preferably, about 1 to about 1.5 moles of pyridine-2-amine per mole of S1b, may be used. Also, about 0.8 moles to about 4 moles of base per mole of S1b, preferably, about 0.9 moles to about 3 moles of base per mole of S1b, and more preferably, about 1 to about 2 moles of base per mole of S1b may be used. In Scheme Two, additional conditions comprise ambient temperatures and pressures. However, higher and lower temperatures and pressures may be used. Currently, temperatures from about −100° C. to about 50° C. may be used; preferably temperatures from about −80° C. to about 20° C. may be used. Currently, pressures from about 10 kilopascals (kPa) to about 1000 kPa may be used; preferably pressures from about 50 kPa to about 150 kPa may be used.

In Scheme Two, S1b may be N-(2-(chloromethyl)-3-(dimethylamino)allylidene)-N-methylmethanaminium chloride, N-(2-(bromomethyl)-3-(dimethylamino)allylidene)-N-methylmethanaminium chloride or N-(2-(iodomethyl)-3-(dimethylamino)allylidene)-N-methylmethanaminium chloride. If desired, mixtures of these three may be used. Currently, N-(2-(chloromethyl)-3-(dimethylamino)allylidene)-N-methylmethanaminium chloride is preferred to be used. Many types of bases may be used such as, for example, triethylamine, N,N-diisopropylethylamine, and N-methylmorpholine; aromatic amines such as pyridine, 2,3-lutidine, 2,4-lutidine, 2,5-lutidine, 2,6-lutidine, 3,4-lutidine, and 3,5-lutidine; lithium diisopropylamide, n-butyllithium, s-butyllithium, sodium amide, sodium hydride, lithium 2,2,6,6-tetramethylpiperidide, and lithium bis(trimethylsilyl)amide. Additionally, organomagnesium halides ($R^{2b}MgX^{2b}$) may be used as bases; where $R^{2b}$ is an alkyl or aryl, such as, for example, methyl, ethyl, propyl, isopropyl, and phenyl, and $X^{2b}$ is a halo, such as, for example Cl, Br, or I. If desired mixtures of these bases may be used. The base could be mixed with pyridyl-2-amine prior to mixing with S1b. Furthermore, other modifications to Scheme Two may be used.

Many types of solvents may be used such as aromatic hydrocarbons (for example, toluene and xylenes), halogenated benzenes (for example, chlorobenzene and 1,2-dichlorobenzene), haloalkanes (for example, dichloromethane and 1,2-dichloroethane), ethers (for example, tetrahydrofuran (THF), 2-methyltetrahydrofuran (2-Me-THF), methyl tert-butyl ether (MTBE), and 1,4-dioxane); esters (for example, ethyl acetate or propyl acetate); and/or other solvents including DMF, N,N-dimethylacetamide (DMA), N-methyl-2-pyrrolidone (NMP), dimethyl sulfoxide (DMSO), acetonitrile, or benzonitrile.

It is preferred when $R^1$ is methyl so that S2b is (E)-N-(3-(dimethylamino)-2-((pyridin-2-ylamino)methyl)allylidene)-N-methylmethanaminium chloride.

When a S1b-substitute is used an S2b-substitute is produced using conditions as indicated above and shown in the scheme below.

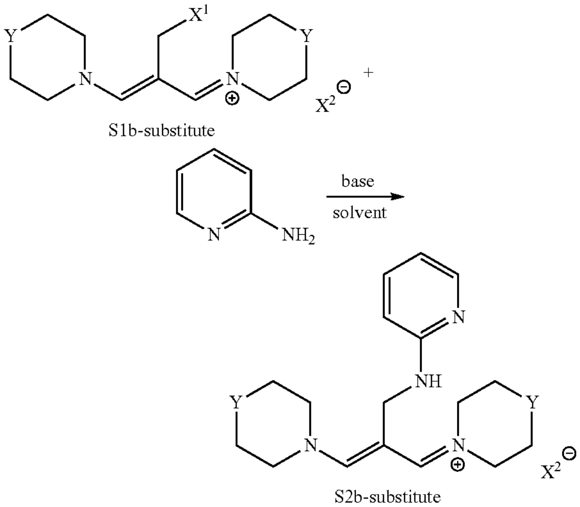

wherein:

$X^1$ is Cl, Br, or I;

each Y is independently $(CH_2)_n$ or O; and n is 0 or 1.

Scheme Three is illustrated as follows

Scheme Three

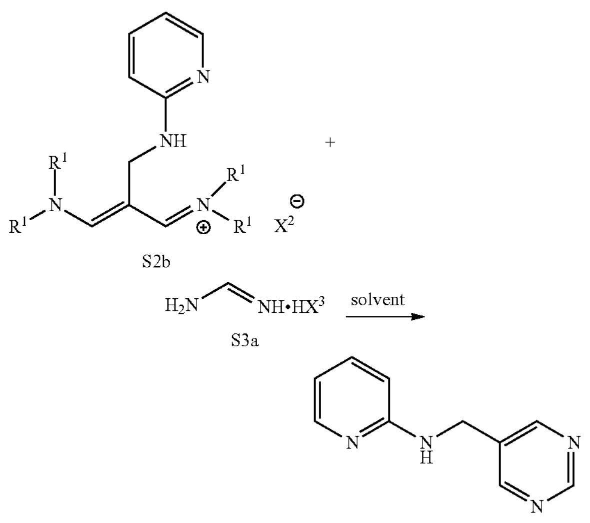

S2b

S3a

S3b wherein $X^3$ is Cl, Br, I, F, $OC(=O)CH_3$, $OC(O)H$, $OC(O)CH_2CH_3$, $H_2PO_4$, or $HSO_4$; and each $R^1$ is methyl, ethyl, or n-propyl.

In Scheme Three, S2b and S3a are mixed under conditions to produce S3b (also known as N-(pyrimidin-5-ylmethyl)pyridin-2-amine). In general, about 0.1 moles to about 10 moles of S3a per mole of S2b, preferably, about 0.5 moles to about 5 moles of S3a per mole of S2b, and more preferably, about 1 to about 2 moles of S3a per mole of S2b may be used. A base is typically used in this mixture. In general, if a base is used, about 0.01 moles to about 6 moles of base per mole of S2b, preferably, about 0.05 moles to about 4 moles of base per mole of S2b, and more preferably, about 0.5 to about 2.5 moles of base per mole of S2b may be used. Many bases may be used, such as, for example, triethylamine, pyridine, 2,3-lutidine, 2,4-lutidine, 2,5-lutidine, 2,6-lutidine, 3,4-lutidine, and 3,5-lutidine, sodium carbonate ($Na_2CO_3$), sodium bicarbonate ($NaHCO_3$), potassium carbonate ($K_2CO_3$), potassium bicarbonate ($KHCO_3$), sodium methoxide ($NaOCH_3$), sodium ethoxide ($NaOCH_2CH_3$), potassium tert-butoxide ($KOC(CH_3)_3$), and if desired, mixtures of such bases may be used. Acids may also be used, such as, for example, p-toluenesulfonic acid monohydrate. In Scheme Three, additional conditions comprise ambient temperatures and pressures. However, higher and lower temperatures and pressures may be used. Currently, temperatures from about 0° C. to about 100° C. may be used; preferably temperatures from about 25° C. to about 80° C. may be used. Currently, pressures from about 10 kilopascals (kPa) to about 1000 kPa may be used; preferably pressures from about 50 kPa to about 150 kPa may be used. S3a may be selected from formamidine acetate, formamidine hydrochloride, formamidine hydrobromide, formamidine sulfate ($H_2N{-}CH{=}NH{\cdot}H_2SO_4$), and mixtures thereof. It is preferred that this mixing be done in the presence of a solvent such as, for example, methanol, ethanol, isopropanol, DMF, DMA, NMP, benzonitrile, DMSO, acetonitrile, THF, and mixtures thereof.

When an S2b-substitute is used under the conditions discussed above for S2b, it will also produce S3b.

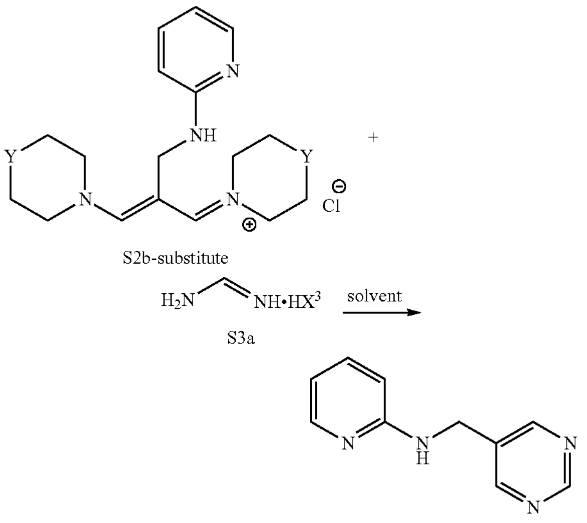

S2b-substitute

S3a

S3b wherein $X^3$ is Cl, Br, I, F, $OC(=O)CH_3$, $OC(O)H$, $OC(O)CH_2CH_3$, $H_2PO_4$, or $HSO_4$;

each Y is independently $(CH_2)_n$ or O; and n is 0 or 1.

EXAMPLES

Example 1A—Preparations of N-(2-(chloromethyl)-3-(dimethylamino)allylidene)-N-methylmethanaminium Chloride

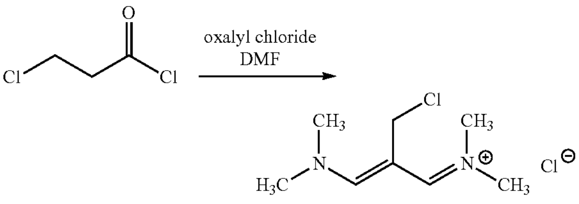

Example 1.1

A 100-milliliter (mL) three-neck round bottom flask, equipped with a stir bar, a condenser with a nitrogen bubbler on the top, a thermocouple, and a pressure-equalizing addition funnel, was charged with anhydrous dimethylformamide (DMF, 11.50 grams (g), 157.32 millimoles (mmol), 4.0 equivalents (equiv)). 3-Chloropropanoyl chloride (5.00 g, 39.38 mmol) was added over two minutes at ambient temperature (25° C.). The mixture was cooled to 0-5° C.; oxalyl chloride (5.0 g, 39.39 mmol, 1.0 equiv) was added dropwise over 30 minutes to maintain the temperature of the reaction mixture below 10° C. After completion of the addition, the reaction mixture was warmed to 25° C. by removing the cooling bath. The reaction mixture was heated slowly to 55-60° C. and stirred at 55-60° C. for an additional three hours. The reaction mixture was cooled to 25° C.; DMF (9.44 g) was added. The resulting mixture was cooled to −5° C. After stirring at −5° C. for two hours, the mixture was filtered under nitrogen atmosphere. The wet cake was rinsed with small amounts of anhydrous DMF and ethyl acetate and was dried in a vacuum oven at ambient temperature to give the title compound (3.80 g, 45.7% yield): $^1H$ NMR (600 MHz, $CD_3CN$) δ 8.16 (s, 2H), 4.64 (s, 2H), 3.48 (s, 6H), 3.37 (s, 6H).

Example 1.2

A 100-mL three-neck round bottom flask, equipped with a stir bar, a condenser with a nitrogen bubbler on the top, a thermocouple, and a pressure-equalizing addition funnel, was charged with anhydrous DMF (11.50 g, 157.32 mmol, 4.0 equiv), and 3-chloropropanoyl chloride (5.00 g, 39.38 mmol) was added over two minutes at ambient temperature (25° C.). The mixture was cooled to 0-5° C.; oxalyl chloride (7.5 g, 59.09 mmol, 1.5 equiv) was added dropwise over 30 minutes, maintaining the temperature of the reaction mixture below 10° C. After completion of the addition, the reaction mixture was warmed to 25° C. by removing the cooling bath. The reaction mixture was heated slowly to 50° C. and stirred at 50° C. for an additional 5 hours. The reaction mixture was cooled to 25° C., and DMF (10 mL, 9.44 g) was added. The resulting mixture was cooled to −5° C. After stirring for two hours at −5° C., the reaction mixture was filtered under nitrogen atmosphere. The wet cake was rinsed with small amounts of anhydrous DMF and ethyl acetate and was dried in a vacuum oven at ambient temperature to give the title compound (4.40 g, 52.9% yield): $^1H$ NMR (600 MHz, $CD_3CN$) δ 8.16 (s, 2H), 4.64 (s, 2H), 3.48 (s, 6H), 3.37 (s, 6H).

Example 1.3

A 100-mL three-neck round bottom flask, equipped with a stir bar, a condenser with a nitrogen bubbler on the top, a thermocouple, and a pressure-equalizing addition funnel, was charged with anhydrous DMF (11.50 g, 157.32 mmol, 4.0 equiv) and 3-chloropropanoyl chloride (5.00 g, 39.38 mmol) was added over two minutes at ambient temperature (25° C.). The mixture was cooled to 0-5° C., and oxalyl chloride (7.5 g, 59.09 mmol, 1.5 equiv) was added dropwise over 30 minutes, maintaining the temperature of the reaction mixture below 10° C. After completion of the addition, the reaction mixture was warmed to 25° C. by removing the cooling bath. The reaction mixture was heated and stirred at 40-45° C. for 22 hours. The reaction mixture was cooled to 25° C., and DMF (10 mL, 9.44 g) was added. The resulting mixture was cooled to −5° C. After stirring for two hours at −5° C., the reaction mixture was filtered under nitrogen atmosphere. The wet cake was rinsed with small amounts of cold anhydrous DMF and ethyl acetate and dried in a vacuum oven at ambient temperature to give the title compound (4.80 g, 57.7% yield): $^1H$ NMR (600 MHz, $CD_3CN$) δ 8.16 (s, 2H), 4.64 (s, 2H), 3.48 (s, 6H), 3.37 (s, 6H).

Example 1.4

A 100-mL three-neck round bottom flask, equipped with a stir bar, a condenser with a nitrogen bubbler on the top, a thermocouple, and a pressure-equalizing addition funnel, was charged with anhydrous DMF (22.89 g, 313.13 mmol, 7.95 equiv), and 3-chloropropanoyl chloride (5.00 g, 39.38 mmol) was added over two minutes at ambient temperature (25° C.). The mixture was cooled to 0-5° C., and oxalyl chloride (5.92 g, 46.64 mmol, 1.2 equiv) was added dropwise over 90 minutes, maintaining the temperature of the reaction mixture below 10° C. After completion of the addition, the reaction mixture was warmed to 25° C. by removing the cooling bath. The reaction mixture was heated and stirred at 40-45° C. for 22 hours. The reaction mixture was cooled and stirred at 25° C. for one hour and at −5° C. for two hours and was filtered under nitrogen atmosphere. The wet cake was rinsed with small amounts of cold anhydrous DMF and ethyl acetate and dried in a vacuum oven at ambient temperature to give the title compound (4.30 g, 51.7% yield): $^1H$ NMR (600 MHz, $CD_3CN$) δ 8.16 (s, 2H), 4.64 (s, 2H), 3.48 (s, 6H), 3.37 (s, 6H).

Example 1.5

A 125-mL four-neck flask, equipped with an overhead stirrer, a condenser with a nitrogen bubbler on the top, a thermocouple, and a syringe pump, was charged with anhydrous DMF (29.20 g, 400 mmol, 4.0 equiv) and was cooled to 0-5° C. Oxalyl chloride (2.78 g, 21.9 mmol, 0.22 equiv) was added by syringe pump over 20 minutes, maintaining the temperature of the reaction mixture below 10° C. The reaction mixture was warmed to 25° C. and was heated to 44-45° C. A mixture of 3-chloropropanoyl chloride (12.70 g, 100 mmol, 1.0 equiv) and oxalyl chloride (12.60 g, 100 mmol, 1.0 equiv) was added via syringe pump over 5 hours at 44-46° C. The resulting reaction mixture was stirred at 44-46° C. until the reaction was complete (overnight). Additional DMF (19.63 g, 268.5 mmol, ~2.7 equiv) was added. The reaction mixture was cooled to 25° C. and stirred at 200 revolutions per minute (rpm) for one hour, was cooled to 0° C. and stirred for two hours and was filtered under nitrogen atmosphere. The wet cake was rinsed with small amounts of cold anhydrous DMF and ethyl acetate and was dried in a vacuum oven at ambient temperature to give the title compound (9.76 g, 46.2% yield): $^1H$ NMR (600 MHz, $CD_3CN$) δ 8.16 (s, 2H), 4.64 (s, 2H), 3.48 (s, 6H), 3.37 (s, 6H).

Example 1.6

Anhydrous DMF (116.94 g, 1.6 moles, 4.0 equiv) was charged into a 250-mL four-neck jacketed reactor equipped with an overhead stirrer, a condenser with a nitrogen bubbler on the top, a thermocouple, and a peristaltic pump. The solvent was heated to 44-45° C. with stirring at 300 rpm under nitrogen atmosphere. A mixture of 3-chloropropanoyl chloride (50.78 g, 400 mmol, 1 equiv) and oxalyl chloride (60.9 g, 480 mmol, 1.2 equiv) was added through the peristaltic pump at such a rate (~13 milliliters per hour (mL/h)) to maintain the reaction temperature in the range of 44-46° C. After completion of the addition (6-8 hours), the resulting mixture was stirred at 44-46° C. overnight (10-15 hours). Additional anhydrous DMF (87.71 g, 1.2 moles, 3 equiv) was added to the reaction mixture. The reaction mixture was heated at 44-46° C. until the reaction was complete (4-8 hours). The reaction mixture was cooled to 20° C. for one hour and to −5° C. for one hour. After stirring at −5° C. for two hours, the reaction mixture was filtered under nitrogen atmosphere. The wet cake was rinsed with cold anhydrous DMF (−5° C., 20-30 mL) and subsequently anhydrous ethyl acetate (50 mL) and dried in a vacuum oven at ambient temperature (20-25° C.) to give the title compound (45.54 g, 53.9% yield).

Example 1.7

Anhydrous DMF (204.6 g, 2.8 moles, 7.0 equiv) was charged into a 250-mL four-neck jacketed reactor equipped with an overhead stirrer, a condenser with a nitrogen bubbler on the top, a thermocouple, and a peristaltic pump. The solvent was heated to 44-45° C. with stirring at 300 rpm under nitrogen atmosphere. A mixture of 3-chloropropanoyl chloride (50.78 g, 400 mmol, 1 equiv) and oxalyl chloride (76.0 g, 600 mmol, 1.5 equiv) was added through the peristaltic pump at such a rate (~13 mL/h) to maintain the reaction temperature in the range of 44-46° C. After completion of the addition (6-8 hours), the resulting mixture was stirred at 44-46° C. overnight (15 hours). The reaction mixture was cooled to 20° C. over 1 hour and to 0 to −5° C. over 1 hour. After stirring at 0 to −5° C. for 1 hour, the reaction mixture was filtered under nitrogen atmosphere. The wet cake was rinsed with cold anhydrous DMF (−5° C., 30 mL) and dried in a vacuum oven at ambient temperature (20-25° C.) to give the title compound (59.3 g, which contained ~5 weight percent (wt %) DMF, 95% purity and 66.6% yield).

Example 1B—Preparations of N-(2-(bromomethyl)-3-(dimethylamino)allylidene)-N-methylmethanaminium Chloride

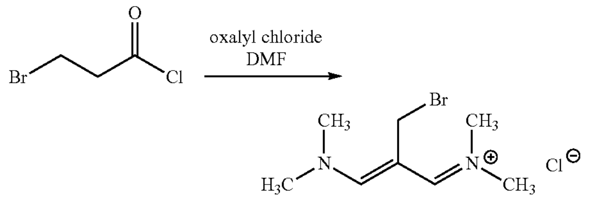

Example 1.8

A 100-mL three-neck round bottom flask, equipped with a stir bar, a condenser with a nitrogen bubbler on the top, a thermocouple, and a pressure-equalizing addition funnel, was charged with anhydrous DMF (8.50 g, 116.22 mmol, 4.0 equiv), and 3-bromopropanoyl chloride (5.00 g, 29.17 mmol, 1.0 equiv) was added over two minutes at ambient temperature (25° C.). The mixture was cooled to 0-5° C., and oxalyl chloride (5.50 g, 43.3 mmol, 1.48 equiv) was added dropwise over 60 minutes, maintaining the temperature of the reaction mixture below 10° C. After completion of the addition, the reaction mixture was warmed to 25° C. by removing the cooling bath. The reaction mixture was heated and stirred at 40° C. for 20 hours. The resulting mixture was cooled to 20° C. and stirred for one hour, was cooled to −5° C. and stirred for one hour and was filtered under nitrogen atmosphere. The wet cake was rinsed with small amounts of cold anhydrous DMF and ethyl acetate and was dried in a vacuum oven at ambient temperature to give the title compound (3.50 g, 46.95% yield): $^1$H NMR (300 MHz, $CD_3CN$) δ 7.95 (s, 2H), 4.64 (s, 2H), 3.49 (s, 6H), 3.36 (s, 6H).

Example 2: Preparations of (E)-N-(3-(dimethylamino)-2-((pyridin-2-ylamino)methyl)allylidene)-N-methylmethanaminium Chloride

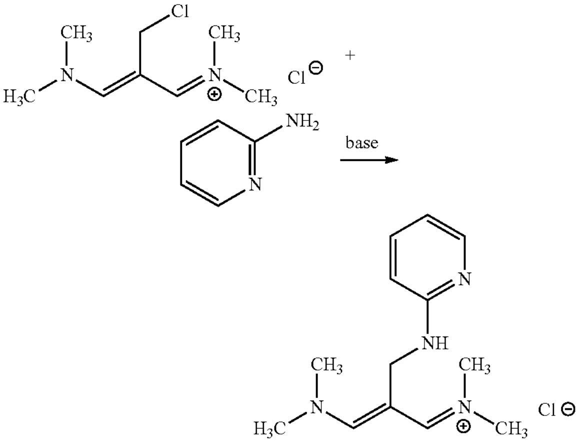

Example 2.1

A solution of pyridin-2-amine (447 mg, 4.74 mmol) in anhydrous THF (10 mL) was cooled to −78° C. under nitrogen atmosphere. A solution of 2.4 M n-butyllithium in hexane (n-BuLi, 2.0 mL, 4.80 mmol, 1.0 equiv) was added dropwise over 30 minutes. The resulting mixture was stirred at −60° C. for 1.5 hours and was added to a suspension of N-(2-(chloromethyl)-3-(dimethylamino)allylidene)-N-methylmethanaminium chloride (1.0 g, 4.74 mmol) in acetonitrile (10 mL) at −45° C. over 30 minutes under nitrogen. The resulting mixture was stirred at −45° C. for 1.5 hours, was warmed to 0° C., and was stirred for 40 minutes. The mixture was filtered, and the wet cake was rinsed with a small amount of acetonitrile. The wet cake was dried in a vacuum oven to afford the title compound (0.70 g, 55% yield): $^1$H NMR (500 MHz, DMSO-$d_6$) δ 8.01 (d, J=6.0 Hz, 1H), 7.72 (s, 2H), 7.42 (t, J=7.1 Hz, 1H), 7.05 (s, 1H), 6.61 (d, J=7.1 Hz, 1H), 6.56 (t, J=6.0 Hz, 1H), 4.02 (d, J=3.7 Hz, 2H), 3.28 (s, 12H). 10% of the title compound was lost in the filtrate as estimated by H NMR spectroscopy.

Example 2.2

To a suspension of N-(2-(chloromethyl)-3-(dimethylamino)allylidene)-N-methylmethanaminium chloride (0.48 g, 2.27 mmol) in acetonitrile (10 mL) at 0° C. were added triethylamine (460 mg, 4.55 mmol, 2.0 equiv) and pyridin-2-amine (213 mg, 2.27 mmol) under nitrogen. The reaction mixture was stirred at 0° C. for 17 hours. The resulting mixture was filtered and rinsed with a small amount of acetonitrile. The wet cake was dried in a vacuum oven to afford the title compound (0.270 g, 44% yield): $^1$H NMR (500 MHz, DMSO-$d_6$) δ 8.01 (d, J=6.0 Hz, 1H), 7.72 (s, 2H), 7.42 (t, J=7.1 Hz, 1H), 7.05 (s, 1H), 6.61 (d, J=7.1 Hz, 1H), 6.56 (t, J=6.0 Hz, 1H), 4.02 (d, J=3.7 Hz, 2H), 3.28 (s, 12H).

Example 2.3

A 50 mL flask was charged with pyridin-2-amine (1.035 g, 11 mmol) and anhydrous THF (8 mL) under nitrogen. The solution was cooled to −15° C. with an ice-salt bath. A solution of 2.15 M n-butyllithium (4.65 mL, 10.0 mmol) was added slowly over 30 minutes, maintaining the reaction temperature between −15 and −10° C. After stirring at −10° C. for 30 minutes, the resulting solution was added dropwise over 20 minutes to a suspension of N-(2-(chloromethyl)-3-(dimethylamino)allylidene)-N-methylmethanaminium chloride (2.111 g, 10.00 mmol) in anhydrous acetonitrile (10 mL) at −13° C. to −10° C., which resulted in an orange slurry. The reaction mixture was stirred at −10° C. for one hour, was warmed to 0° C., and was filtered under nitrogen atmosphere. The wet cake was rinsed with anhydrous THF (20 mL) and hexane (10 mL). The wet cake was dried under vacuum to give the title compound (1.97 g, 71.9% yield and 98% purity estimated by Q-$^1$H NMR).

Example 2.4

A solution of pyridin-2-amine (2.23 g, 23.7 mmol, 1.0 equiv) in anhydrous THF (50 mL) was cooled to −10° C. under nitrogen atmosphere, and a solution of n-BuLi in hexane (2.4 M, 8.9 mL, 21.3 mmol, 0.9 equiv) was added dropwise over 20 minutes. After stirring for 1.5 hours at −10° C., the resulting solution was added over 30 minutes to a stirring suspension of N-(2-(chloromethyl)-3-(dimethylamino)allylidene)-N-methylmethanaminium chloride (5.00 g, 23.7 mmol) in anhydrous acetonitrile (50 mL) at −10° C. The resulting yellow suspension was stirred at −10° C. for 3 hours and filtered under nitrogen atmosphere. The wet cake was rinsed with cold THF (20 mL) and dried to give a yellow solid (5.30 g, which contained 89 wt % of the title compound and 11 wt % of lithium chloride (LiCl)). The yield of the title compound was 74.3%.

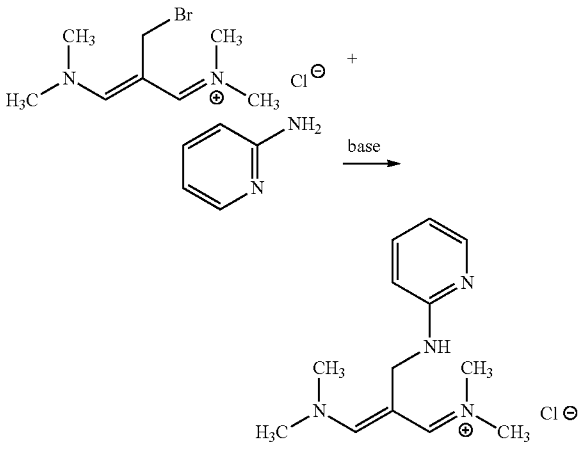

Example 2.5

To a suspension of N-2-(bromomethyl)-3-(dimethylamino)allylidene)-N-methylmethanaminium chloride (0.48 g, 1.88 mmol) in acetonitrile (10 mL) at 0° C. were added triethylamine (380 mg, 3.76 mmol, 2.0 equiv) and pyridin-2-amine (177 mg, 1.88 mmol) under nitrogen. The reaction mixture was stirred at 0° C. for 16 hours. The resulting mixture was filtered and was rinsed with a small amount of acetonitrile. The wet cake was dried in a vacuum oven to afford the title compound (0.140 g, 28% yield): $^1$H NMR (500 MHz, DMSO-$d_6$) δ 8.01 (d, J=6.0 Hz, 1H), 7.72 (s, 2H), 7.42 (t, J=7.1 Hz, 1H), 7.05 (s, 1H), 6.61 (d, J=7.1 Hz, 1H), 6.56 (t, J=6.0 Hz, 1H), 4.02 (d, J=3.7 Hz, 2H), 3.28 (s, 12H).

Example 3: Preparations of N-(pyrimidin-5-ylmethyl)pyridin-2-amine

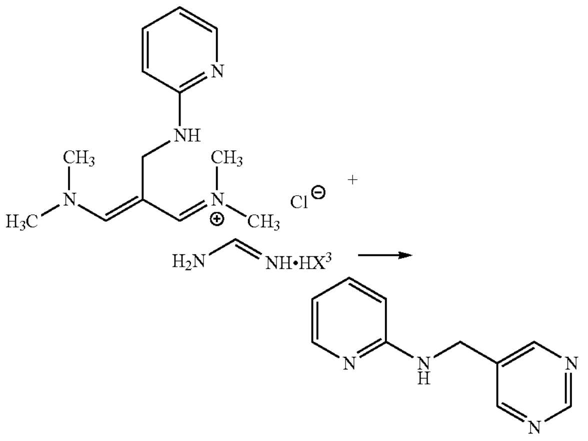

Example 3.1

To a solution of (E)-N-(3-(dimethylamino)-2-((pyridin-2-ylamino)methyl)allylidene)-N-methylmethanaminium chloride (621 mg, 2.31 mmol) in ethanol (10 mL) was added formamidine acetate (265 mg, 2.54 mmol). The mixture was stirred at 80° C. for 16 hours and was concentrated under vacuum. The residue was purified by flash column chromatography on silica gel, eluting with a gradient of 0-3% methanol (MeOH) in dichloromethane (DCM) to afford the title compound (0.250 g, 56% yield).

Example 3.2

A 50-mL three-neck round bottom flask, equipped with a stir bar, a condenser with a nitrogen bubbler on the top, and a thermocouple, was charged with anhydrous DMF (40 mL), (E)-N-(3-(dimethylamino)-2-((pyridin-2-ylamino)methyl)allylidene)-N-methylmethanaminium chloride (882 mg, 3.28 mmol), formamidine acetate (341 mg, 3.28 mmol), and potassium carbonate ($K_2CO_3$, 906 mg, 6.56 mmol). The mixture was stirred at 70° C. for 16 hours. After evaporation of solvent, the residue was purified by flash column chromatography on silica gel, eluting with a gradient of 0-3% MeOH in DCM, to afford the title compound (0.556 g, 91.0% yield).

Example 3.3

To a mixture of (E)-N-(3-(dimethylamino)-2-((pyridin-2-ylamino)methyl)allylidene)-N-methylmethanaminium chloride (5.00 g, 85 wt % purity, which contained 15 wt % LiCl, 18.7 mmol) and formamidine acetate (1.94 g, 18.7 mmol) in anhydrous MeOH (50.0 mL) was added anhydrous potassium carbonate ($K_2CO_3$, 5.16 g, 37.4 mmol, 2 equiv) under nitrogen atmosphere. The reaction mixture was heated and stirred at 40° C. until (E)-N-(3-(dimethylamino)-2-((pyridin-2-ylamino)methyl)allylidene)-N-methylmethanaminium chloride was consumed as indicated by highperformance liquid chromatography (HPLC) (1.5 hours). The reaction mixture was cooled to room temperature and filtered. The wet cake was rinsed with MeOH (10 mL). Analysis of the filtrate by H NMR spectroscopy indicated 98% in-pot yield of the title compound. The filtrate was concentrated under reduced pressure by rotary evaporation to give a residue (3.0 g). The residue was recrystallized from ethyl acetate and hexane to give the title compound (2.67 g, 90.5% yield).

Example 4: Preparation f N-(2-(chloromethyl)-3-(dimethylamino)allylidene)-N-methylmethanaminium Chloride

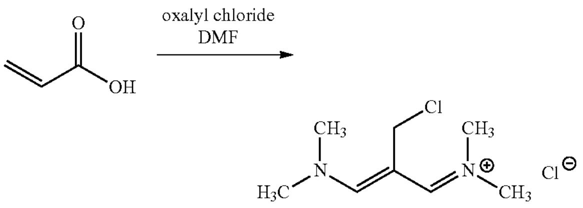

Anhydrous N,N-dimethylformamide (DMF, 116.94 g, 1.6 moles, 4.0 equiv) was charged into a 250-mL four-neck jacketed reactor equipped with an overhead stirrer, a condenser (with a nitrogen blanket on the top), and a thermocouple and was heated to 44 to 45° C. with stirring at 300 rpm under nitrogen atmosphere. Acrylic acid (28.82 g, 400 mmol, 1 equiv) and oxalyl chloride (111.70 g, 880 mmol, 2.2 equiv) were added simultaneously through two syringe pumps over a period of time at such rates to maintain the reaction temperature in the range of 44 to 46° C. After completion of the addition (6-8 hours), the resulting mixture was stirred at 44-46° C. overnight (10-15 hours). Additional anhydrous DMF (87.71, 1.2 moles, 3.0 equiv) was added to the reaction mixture. The reaction mixture was kept at 44-46° C. until the reaction was complete (4-8 hours). The reaction mixture was cooled to 0 to −5° C. over 3 hours. After holding at 0 to −5° C. for 2 hours, the reaction mixture was filtered under nitrogen atmosphere. The wet cake was rinsed with cold anhydrous DMF (0 to −5° C., 20-30 mL) and subsequently anhydrous tetrahydrofuran (50 mL), and was dried in a vacuum oven at ambient temperature (20 to 25° C.) to give the title compound (38.5 g, 45.6% yield).

Considering the above the following additional details (D) are provided.

1D. A process comprising mixing S1a, N,N-diallylformamide ("DAF"), and oxalyl chloride ($(COCl)_2$), under conditions to produce S1b

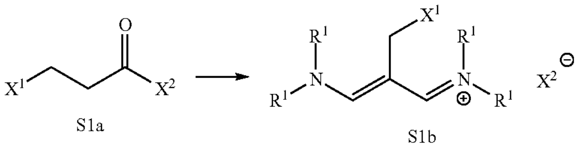

S1a S1b wherein $X^1$ is Cl, Br, or I;

$X^2$ is F, Cl, Br, I, or OH;

each $R^1$ is methyl, ethyl, or n-propyl.

2D. A process according to 1D wherein $X^1$ is Cl.

3D. A process according to 1D wherein $X^1$ is Br.

4D. A process according to 1D wherein $X^1$ is I.

5D. A process according to 1D, 2D, 3D, or 4D wherein $X^2$ is F.

6D. A process according to 1D, 2D, 3D, or 4D wherein $X^2$ is Cl.

7D. A process according to 1D, 2D, 3D, or 4D wherein $X^2$ is Br.

8D. A process according to 1D, 2D, 3D, or 4D wherein $X^2$ is I.

9D. A process according to 1D, 2D, 3D, or 4D wherein $X^2$ is OH.

10D. A process according to any of the previous details wherein about 2 moles to about 20 moles of DAF per mole of S1a is used.

11D. A process according to any of the previous details wherein about 3 moles to about 15 moles of DAF per mole of S1a is used.

12D. A process according to any of the previous details wherein about 4 to about 10 moles of DAF per mole of S1a is used.

13D. A process according to any of the previous details wherein about 0.5 moles to about 5 moles of oxalyl chloride per mole of S1a is used.

14D. A process according to any of the previous details wherein about 0.8 moles to about 4 moles of oxalyl chloride per mole of S1a is used.

15D. A process according to any of the previous details wherein about 1 mole to about 3 moles of oxalyl chloride per mole of S1a is used.

16D. A process according to any of the previous details wherein conditions comprise ambient temperatures and pressures.

17D. A process according to any of the previous details wherein conditions comprise temperatures from about −10° C. to about 80° C.

18D. A process according to any of the previous details wherein conditions comprise temperatures from about −5° C. to about 60° C.

19D. A process according to any of the previous details wherein conditions comprise pressures from about 10 kilopascals (kPa) to about 1000 kPa.

20D. A process according to any of the previous details wherein conditions comprise pressures from about 50 kPa to about 150 kPa.

21D. A process according to any of the previous details wherein S1a is 3-chloropropanoyl chloride, 3-chloropropanoyl bromide, 3-chloropropanoyl fluoride, 3-chloropropanoyl iodide, 3-bromopropanoyl chloride, 3-bromopropanoyl bromide, 3-bromopropanoyl fluoride, 3-bromopropanoyl iodide, 3-iodopropanoyl chloride, 3-iodopropanoyl iodide, 3-iodopropanoyl bromide, 3-iodopropanoyl fluoride, 3-chloropropanoic acid, 3-bromopropanoic acid, 3-iodopropanoic acid, or mixtures thereof.

22D. A process according to any of the previous details wherein S1a is 3-chloropropanoyl chloride.

23D. A process according to any of the previous details wherein a substitute for oxalyl chloride ($(COCl)_2$) is selected from phosphoryl chloride ($POCl_3$), thionyl chloride ($SOCl_2$), phthaloyl chloride ($C_6H_4$-1,2-$(COCl)_2$), or mixtures thereof.

24D. A process according to any of the previous details wherein a substitute for N,N-dialkyl formamide is selected from piperidine-1-carbaldehyde, pyrrolidine-1-carbaldehyde, or morpholine-4-carbaldehyde is used so that an S1b-substitute is produced

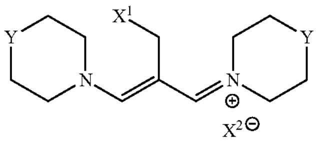

S1b-substitute wherein:

$X^1$ is Cl, Br, or I;

each Y is independently $(CH_2)_n$ or O; and n is 0 or 1.

24.2D A process according to details 1D, and 10D through 20D wherein S1a is substituted with acrylic acid.

24.4D A process according to detail 24.5 wherein about 1.5 moles to about 5 moles of oxalyl chloride per mole of acrylic acid is used.

24.6D A process according to detail 24.5 wherein about 1.8 moles to about 4 moles of oxalyl chloride per mole of acrylic acid is used.

24.8D A process according to detail 24.5 wherein about 2 to about 3 moles of oxalyl chloride per mole of acrylic acid is used.

25D. A process comprising mixing S1b, pyridine-2-amine and a base in the presence of a solvent, under conditions to produce S2b.

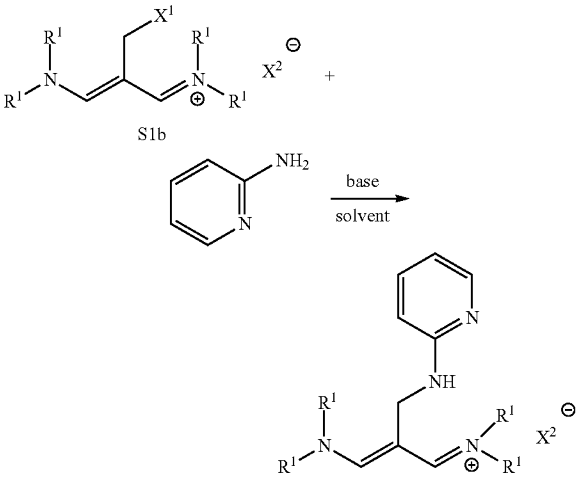

S1b

S2b wherein $X^1$ is Cl, Br, or I; and each $R^1$ is methyl, ethyl, or n-propyl.

26D. A process according to 25D wherein $X^1$ is Cl.

27D. A process according to 25D wherein $X^1$ is Br.

28D. A process according to 25D wherein $X^1$ is I.

29D. A process according to any of the previous details 25D through 28D wherein about 0.8 moles to about 2 moles of pyridine-2-amine per mole of S1b is used.

30D. A process according to any of the previous details 25D through 28D wherein about 0.9 moles to about 1.8 moles of pyridine-2-amine per mole of S1b is used.

31D. A process according to any of the previous details 25D through 28D wherein about 1 to about 1.5 moles of pyridine-2-amine per mole of S1b is used.

32D. A process according to any of the previous details 25D through 31D wherein about 0.8 moles to about 4 moles of base per mole of S1b is used.

33D. A process according to any of the previous details 25D through 31D wherein about 0.9 moles to about 3 moles of base per mole of S1b is used.

34D. A process according to any of the previous details 25D through 31D wherein about 1 to about 2 moles of base per mole of S1b is used.

35D. A process according to any of the previous details 25D through 34D wherein conditions comprise ambient temperatures and pressures.

36D. A process according to any of the previous details 25D through 34D wherein conditions comprise temperatures from about −100° C. to about 50° C.

37D. A process according to any of the previous details 25D through 34D wherein conditions comprise temperatures from about −80° C. to about 20° C.

38D. A process according to any of the previous details 25D through 34D wherein conditions comprise pressures from about 10 kilopascals (kPa) to about 1000 kPa.

39D. A process according to any of the previous details 25D through 34D wherein conditions comprise pressures from about 50 kPa to about 150 kPa.

40D. A process according to any of the previous details 25D through 39D wherein S1b is N-(2-(chloromethyl)-3-(dimethylamino)allylidene)-N-methylmethanaminium chloride, N-(2-(bromomethyl)-3-(dimethylamino)allylidene)-N-methylmethanaminium chloride, N-(2-(iodomethyl)-3-(dimethylamino)allylidene)-N-methylmethanaminium chloride, or mixtures thereof.

41D. A process according to any of the previous details 25D through 40D wherein S1b is N-(2-(chloromethyl)-3-(dimethylamino)allylidene)-N-methylmethanaminium chloride.

42D. A process according to any of the previous details 25D through 40D wherein said base is selected from the group consisting of triethylamine, N,N-diisopropylethylamine, lithium diisopropylamide, n-butyllithium, s-butyllithium, sodium amide, sodium hydride, lithium bis(trimethylsilyl)amide, lithium 2,2,6,6-tetramethylpiperidide, and mixtures thereof.

43D. A process according to any of the previous details 25D through 40D wherein said base is an organomagnesium halide of formula ($R^{2b}MgX^{2b}$) wherein $R^{2b}$ is an $(C_1$-$C_4)$alkyl or $(C_6$-$C_{10})$ aryl and $X^{2b}$ is Cl, Br, or I.

44D. A process according to 43D wherein said alkyl is methyl, ethyl, propyl, or isopropyl.

45D. A process according to any of the previous details 25D through 44D wherein a S1b-substitute for S1b is used to produce an S2b-substitute.

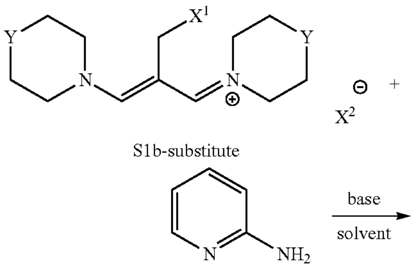

S1b-substitute

-continued

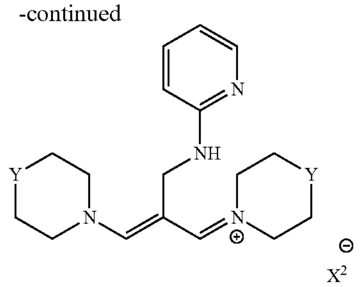

S2b-substitute

46D. A process according to any of the previous details 25D through 45D wherein said solvent is an aromatic hydrocarbon, a halogenated benzene, a haloalkane, an ether, an ester, or mixtures thereof.

47D. A process according to any of the previous details 25D through 46D wherein said solvent is, toluene, xylene, chlorobenzene, 1,2-dichlorobenzene, dichloromethane, 1,2-dichloroethane, tetrahydrofuran, 2-methyltetrahydrofuran, methyl tert-butyl ether, 1,4-dioxane, ethyl acetate, propyl acetate, DMF, N,N-dimethylacetamide, N-methyl-2-pyrrolidone, dimethyl sulfoxide, acetonitrile, benzonitrile, or mixtures thereof.

48D. A process comprising mixing S2b and S3a under conditions to produce S3b also known as N-(pyrimidin-5-ylmethyl)pyridin-2-amine.

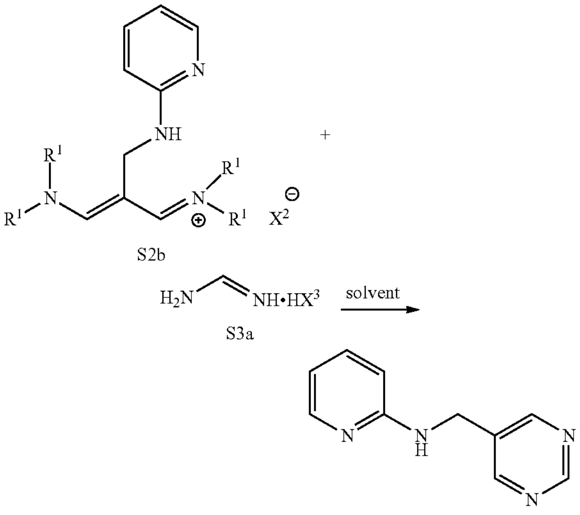

S2b S3a S3b wherein $X^3$ is Cl, Br, I, F, OC(=O)$CH_3$, OC(O)H, OC(O)$CH_2CH_3$, $H_2PO_4$, or $HSO_4$; and each $R^1$ is methyl, ethyl, or n-propyl.

49D. A process according to 48D wherein about 0.1 moles to about 10 moles of S3a per mole of S2b is used.

50D. A process according to 49D wherein about 0.5 moles to about 5 moles of S3a per mole of S2b is used.

51D. A process according to 49D wherein about 1 to about 2 moles of S3a per mole of S2b is used.

52D. A process according to any of the previous details 48D through 51D wherein a base is used and about 0.01 moles to about 6 moles of base per mole of S2b is used.

53D. A process according to any of the previous details 48D through 52D wherein a base is used and about 0.05 moles to about 4 moles of base per mole of S2b is used.

54D. A process according to any of the previous details 48D through 52D wherein a base is used and about 0.5 to about 2.5 moles of base per mole of S2b is used.

55D. A process according to details 52D through 54D wherein said base is selected from the group consisting of triethylamine, $Na_2CO_3$, $NaHCO_3$, $K_2CO_3$, $KHCO_3$, $NaOCH_3$, $NaOCH_2CH_3$, $KOC(CH_3)_3$, and mixtures thereof.

56D. A process according to any of the previous details 48D through 55D wherein conditions comprise temperatures from about 0° C. to about 100° C.

57D. A process according to any of the previous details 48D through 56D wherein conditions comprise temperatures from about 25° C. to about 80° C.

58D. A process according to any of the previous details 48D through 57D wherein conditions comprise pressures from about 10 kilopascals (kPa) to about 1000 kPa.

59D. A process according to any of the previous details 48D through 57D wherein conditions comprise pressures from about 50 kPa to about 150 kPa.

We claim:

1. A process comprising (1) mixing S1a, N,N-dialkylformamide and oxalyl chloride ($(COCl)_2$), under conditions to produce S1b

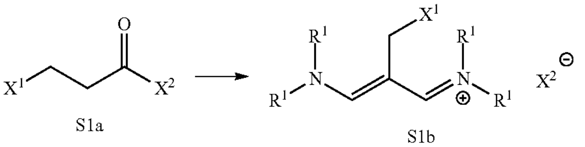

S1a S1b wherein $X^1$ is Cl, Br, or I; and $X^2$ in S1a is F, Cl, Br, I, or OH; $X^2$ in S1b is F, Cl, Br, or I; and each $R^1$ is methyl, ethyl, or n-propyl; followed by (2) mixing S1b, pyridine-2-amine, and a base, in the presence of a solvent, under conditions to produce S2b

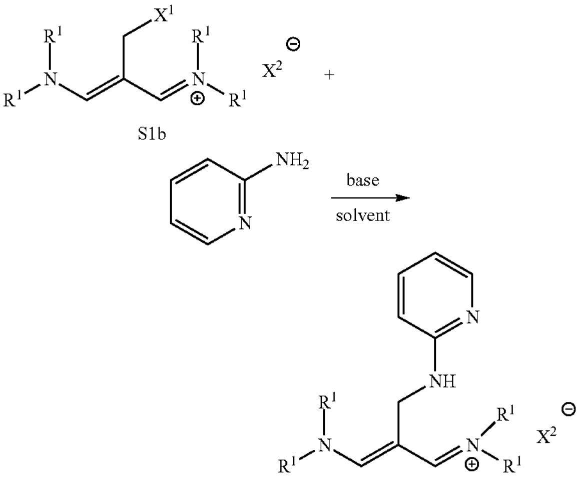

S1b S2b wherein
$X^2$ in S2b is F, Cl, Br, or I;
followed by
(3) mixing S2b, S3a, and a base, under conditions to produce S3b
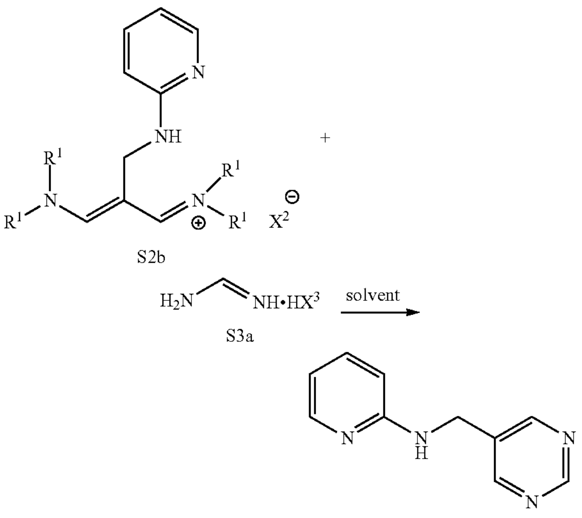
S2b
S3a
S3b
wherein
$X^3$ is Cl, Br, I, F, $OC(=O)CH_3$, $OC(O)H$, $OC(O)CH_2CH_3$, $H_2PO_4$, or $HSO_4$.
* * * * *